(12) United States Patent
Hess

(10) Patent No.: US 7,515,959 B2
(45) Date of Patent: Apr. 7, 2009

(54) DELIVERY OF CRT THERAPY DURING AT/AF TERMINATION

(75) Inventor: Michael F. Hess, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 521 days.

(21) Appl. No.: 11/096,511

(22) Filed: Mar. 31, 2005

(65) Prior Publication Data

US 2006/0224193 A1 Oct. 5, 2006

(51) Int. Cl.
*A61N 1/362* (2006.01)
(52) U.S. Cl. ........................................... 607/14
(58) Field of Classification Search ............... None
See application file for complete search history.

(56) References Cited

U.S. PATENT DOCUMENTS

| | | | |
|---|---|---|---|
| 4,316,472 A | 2/1982 | Mirowski et al. |
| 4,375,817 A | 3/1983 | Engle et al. |
| 4,384,585 A | 5/1983 | Zipes |
| 4,577,633 A | 3/1986 | Berkovits et al. |
| 4,587,970 A | 5/1986 | Holley et al. |
| 4,727,380 A | 2/1988 | Miura et al. |
| 4,727,877 A | 3/1988 | Kallok |
| 4,800,883 A | 1/1989 | Winstrom |
| 4,830,006 A | 5/1989 | Haluska et al. |
| 4,880,005 A | 11/1989 | Pless et al. |
| 4,932,406 A | 6/1990 | Berkovits |
| 4,944,298 A | 7/1990 | Sholder |
| 4,949,719 A | 8/1990 | Pless et al. |
| 4,953,551 A | 9/1990 | Mehra et al. |
| 5,117,824 A | 6/1992 | Keimel et al. |
| 5,144,949 A | 9/1992 | Olson |
| 5,163,427 A | 11/1992 | Keimel |
| 5,188,105 A | 2/1993 | Keimel |
| 5,292,340 A | 3/1994 | Crosby et al. |
| 5,318,594 A | 6/1994 | Limousin et al. |
| 5,792,192 A | 8/1998 | Lu |
| 5,792,203 A | 8/1998 | Schroeppel |
| 5,814,083 A | 9/1998 | Hess et al. |
| 5,902,324 A | 5/1999 | Thompson et al. |

(Continued)

FOREIGN PATENT DOCUMENTS

EP 1038548 A2 9/2000

(Continued)

*Primary Examiner*—Carl H. Layno
*Assistant Examiner*—Jon-Eric Morales
(74) *Attorney, Agent, or Firm*—Stephen W. Bauer

(57) ABSTRACT

In some embodiments, a method for operating a cardiac rhythm management device may include one or more of the following steps: (a) sensing atrial depolarizations through an implanted atrial electrode, (b) administering a sequential CRT pacing therapy in a sequential CRT pacing mode to a left and right ventricle of a heart of a patient via implanted ventricular electrodes in a sequential bi-ventricular fashion, (c) switching from the sequential CRT pacing mode to a simultaneous CRT pacing mode, (d) administering a simultaneous CRT pacing therapy in the simultaneous CRT pacing mode to the left and right ventricle in a simultaneous bi-ventricular fashion, (e) analyzing the sensed atrial depolarizations to detect the presence of an atrial arrhythmia, (f) analyzing the sensed atrial depolarizations while in the sequential CRT pacing mode to detect the presence of atrial arrhythmia, and (g) sensing ventricular depolarizations of the left and the right ventricle.

22 Claims, 8 Drawing Sheets

U.S. PATENT DOCUMENTS

| | | |
|---|---|---|
| 6,122,545 A | 9/2000 | Stuble et al. |
| 6,370,427 B1 | 4/2002 | Alt et al. |
| 6,735,472 B2 | 5/2004 | Helland |
| 6,748,268 B1 | 6/2004 | Helland et al. |
| 2002/0082660 A1* | 6/2002 | Stahmann et al. ............. 607/14 |
| 2003/0195572 A1 | 10/2003 | Bocek et al. |

FOREIGN PATENT DOCUMENTS

| | | |
|---|---|---|
| WO | WO9218198 | 10/1992 |
| WO | WO9528987 | 11/1995 |
| WO | WO9528988 | 11/1995 |
| WO | WO02051496 A2 | 7/2002 |

* cited by examiner

DELIVERY OF CRT THERAPY DURING AT/AF TERMINATION

FIELD

The disclosure generally pertains to embodiments for cardiac rhythm management. In particular, some embodiments relate to methods and apparatuses for providing cardiac resynchronization therapy (CRT) along with atrial therapies such as cardioversion and anti-tachy pacing.

BACKGROUND SECTION

In the context of dual chamber pacing, a variety of mode switching features have been developed which detect an excessively rapid atrial rhythm and, in response, cause the pacemaker to switch from an atrial synchronized pacing mode, such as DDD, to a non-synchronized mode such as VVI or DDI. Such mode switching features are disclosed in U.S. Pat. No. 5,144,949, by Olson, U.S. Pat. No. 5,318,594, by Limousin et al., U.S. Pat. No. 4,944,298, by Sholder, U.S. Pat. No. 5,292,340, by Crosby et al. and U.S. Pat. No. 4,932,406 by Berkovits, all incorporated herein by reference in their entireties. In such devices, the primary purpose of the mode switch is to prevent the pacemaker from tracking a non-physiologic atrial rate.

It is common in dual chamber pacing with both atrial and ventricular sensing leads for the atrial sensing channel to be blanked after a ventricular event for a specified blanking interval. This is done to avoid oversensing, including far-field sensing of ventricular depolarizations by the atrial sensing lead. The blanking periods can complicate the detection of atrial tachycardia or atrial flutter since the blanking periods can block detection of some atrial events. Further, a dual chamber device with pacing pulse timing optimized to improve patient hemodynamics may have sequential right and left ventricular pacing pulses that are often separated in time by as much as 80 ms. The sequential pacing of such devices increases the atrial blanking period and, thereby, increases the difficulty of detecting AF or atrial flutter.

BRIEF SUMMARY OF THE INVENTION

The present invention is an implantable medical device (IMD) that provides cardiac resynchronization therapy (CRT). Sequential and simultaneous CRT including atrial pacing are selectively implanted based on continuous monitoring cardiac rhythm to detect arrhythmias.

DETAILED DESCRIPTION OF VARIOUS EMBODIMENTS

Figure 1:
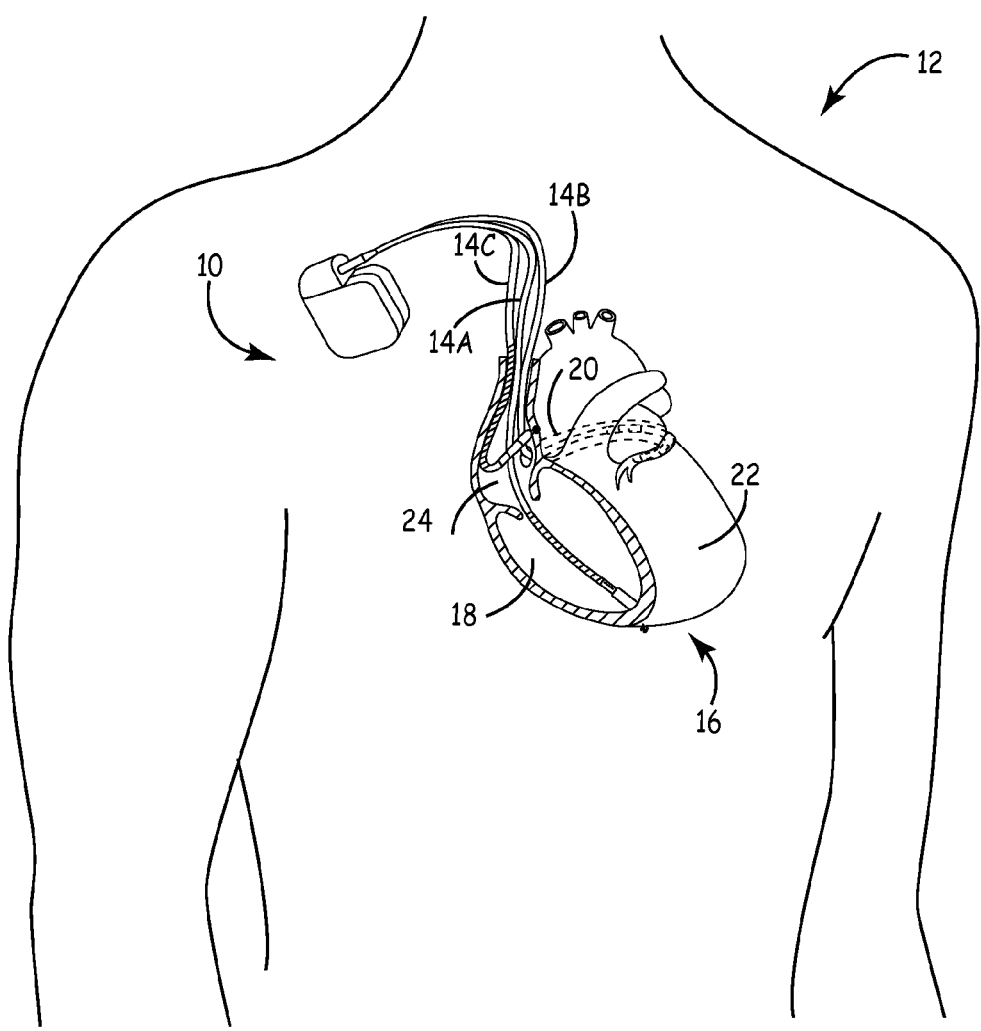
FIG. 1 is a conceptual diagram illustrating an exemplary implantable medical device implanted in a patient that selectively switches to atrial pacing or defibrillation during delivery of pacing pulses according to sensed atrial abnormalities.

The following discussion is presented to enable a person skilled in the art to make and use the present invention. Various modifications to the illustrated embodiments will be readily apparent to those skilled in the art, and the generic principles herein may be applied to other embodiments and applications without departing from the present invention. Thus, the present invention is not intended to be limited to embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the claimed invention. Skilled artisans will recognize the examples provided herein have many useful alternatives and fall within the scope of the present invention.

With reference to FIG. 1, a conceptual diagram illustrating an exemplary implantable medical device implanted in a patient that selectively provides atrial pacing or defibrillation along with the delivery of a CRT therapy according to sensed atrial abnormalities is shown.

According to certain embodiments of the invention, IMD 10 selectively provides right atrial delivery of pacing pulses or defibrillation pulses during periods of bi-ventricular pacing based on an algorithm in order to eliminate atrial arrhythmias and improve the hemodynamic performance of the heart 16 of patient 12. IMD 10, as shown in FIG. 1, takes the form of a pacemaker or defibrillator providing a CRT therapy.

IMD 10 includes leads 14A, 14B, and 14C (collectively "leads 14") that extend into heart 16. More particularly, right ventricular (RV) lead 14A extends through one or more veins (not shown), the superior vena cava (not shown), and right atrium 24, and into right ventricle 18. Left ventricular (LV) coronary sinus lead 14B extends through the veins, the vena cava, right atrium 24, and into the coronary sinus 20 to a point adjacent to the free wall of left ventricle 22 of heart 16. Right atrial (RA) lead 14C extends through the veins and vena cava, and into the right atrium 24 of heart 16.

IMD 10 senses electrical signals attendant to the depolarization and repolarization of heart 16, and provides pacing pulses via electrodes (not shown) located on leads 14. IMD 10 can also provide cardioversion or defibrillation pulses via electrodes located on leads 14. The sense/pace electrodes located on leads 14 may be unipolar or bipolar, as is well known in the art.

During periods of possible atrial fibrillation or tachycardia, IMD 10 can deliver simultaneous bi-ventricular pacing pulses or suspend the bi-ventricular pacing according to an algorithm to stabilize the atrial rate. As will be described in greater detail below, IMD 10 can receive a signal, e.g., an electrogram that represents electrical activity within heart 16, and process the signal to detect abnormalities in atrium 24. In response, IMD 10 can synchronize or suspend the sequential bi-ventricular pacing to reduce any "blanking" periods. With a reduced blanking period, IMD 10 can sense signals in the atrium 24 over a greater percentage of a heart cycle, thus allowing IMD 10 to better determine if an atrial abnormality is occurring. Blanking periods are used to prevent saturation of the sense amplifier or to prevent oversensing. The sensing electrode can be blanked for a specified blanking interval by disabling the sense amplifier when a pace is delivered.

The configuration of IMD 10 and leads 14 illustrated in FIG. 1 is merely exemplary. IMD 10 may be coupled any number of leads 14 that extend to a variety of positions within or outside of heart 16. For example, at least some of leads 14 may be epicardial leads. Further, IMD 10 need not be implanted within patient 12, but may instead be coupled with subcutaneous leads 14 that extend through the skin of patient 12 to a variety of positions within or outside of heart 16.

Figure 2:
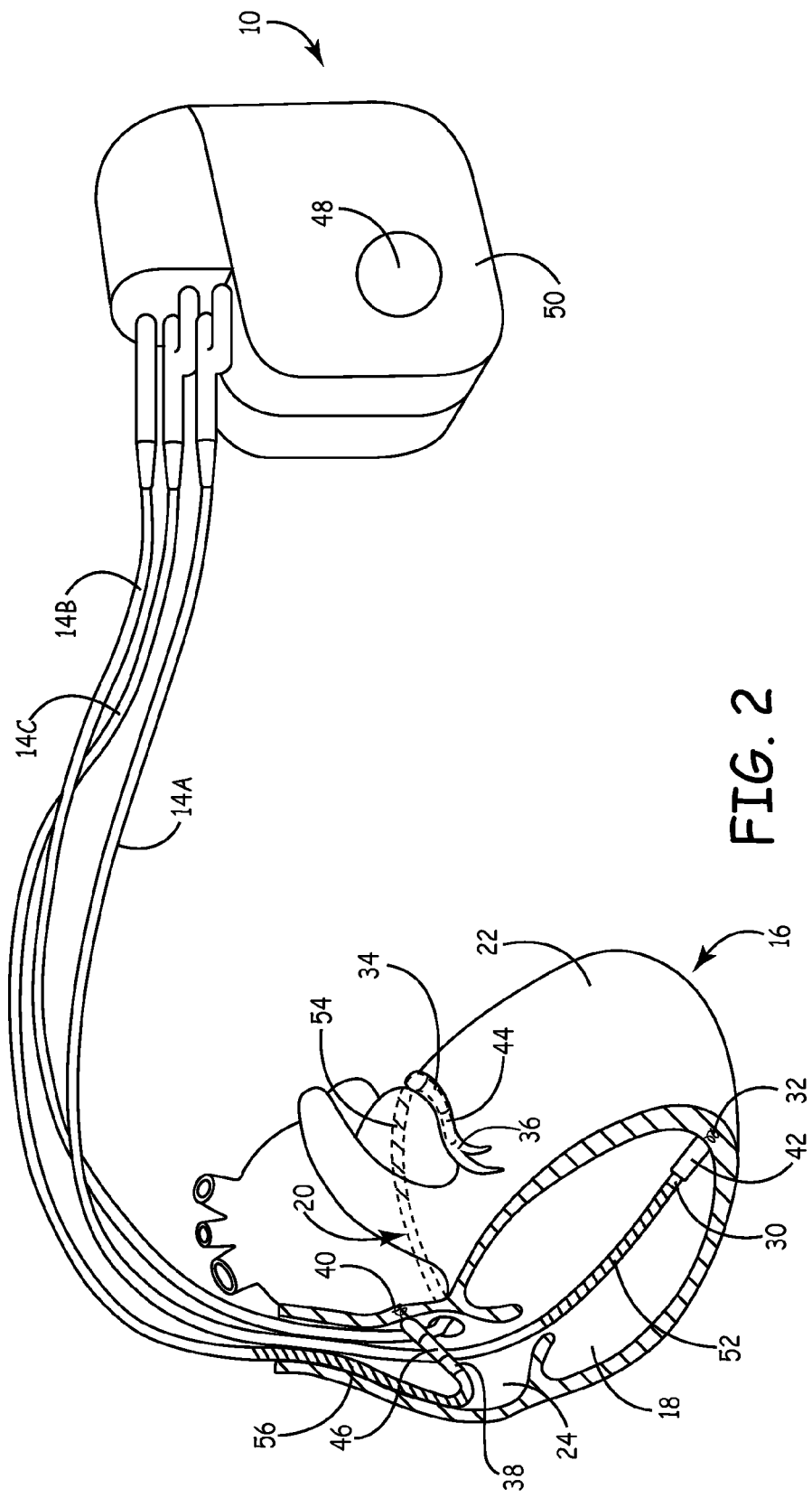
FIG. 2 is conceptual diagram further illustrating the implantable medical device of FIG. 1 and the heart of the patient.

With reference to FIG. 2, conceptual diagram further illustrating the implantable medical device of FIG. 1 and the heart of the patient is shown. Each of leads 14 includes an elongated insulative lead body carrying a number of concentric coiled conductors separated from one another by tubular insulative sheaths. Located adjacent distal end of leads 14A, 14B, and 14C are bipolar electrodes 30 and 32, 34 and 36, and 38 and 40 respectively. Electrodes 30, 34, and 38 may take the form of ring electrodes, and electrodes 32, 36, and 40 may take the form of extendable helix tip electrodes mounted retractably within insulative electrode heads 42, 44, and 46, respectively. Each of the electrodes 30-40 is coupled to one of the coiled conductors within the lead body of its associated lead 14.

Sense/pace electrodes 30, 32, 34, 36, 38, and 40 sense electrical signals attendant to the depolarization and repolarization of heart 16. The electrical signals are conducted to IMD 10 via leads 14. Sense/pace electrodes 30, 32, 34, 36, 38 and 40 further deliver pacing pulses to cause depolarization of cardiac tissue in the vicinity thereof. IMD 10 may also include one or more housing electrodes, such as housing electrode 48, formed integral with an outer surface of the hermetically sealed housing 50 of IMD 10. Any of electrodes 30, 32, 34, 36, 38, and 40 may be used for unipolar sensing or pacing in combination with housing electrode 48.

The invention is not limited to the sense/pace electrode locations illustrated in FIG. 2. For example, in the example embodiment illustrated in FIG. 2, tip electrode 32 of RV lead 14A is disposed in the apical region of right ventricle 18. However, in other embodiments, tip electrode 32 may be located near the pulmonary artery outflow tract (not shown) or the bundle of His. Such alternative locations may provide improved response or conduction, and thus hemodynamically beneficial, contraction of ventricles 18 and 22 through delivery of pacing at a single location by delivering pulses near the specialized conduction system of heart 16.

Leads 14A, 14B and 14C may also, as shown in FIG. 2, include elongated coil electrodes 52, 54 and 56, respectively. IMD 10 may deliver defibrillation or cardioversion shocks to heart 16 via defibrillation electrodes 52-56. Defibrillation electrodes 52-56 may be fabricated from platinum, platinum alloy or other materials known to be usable in implantable defibrillation electrodes, and can be about 5 cm in length.

Figure 3:
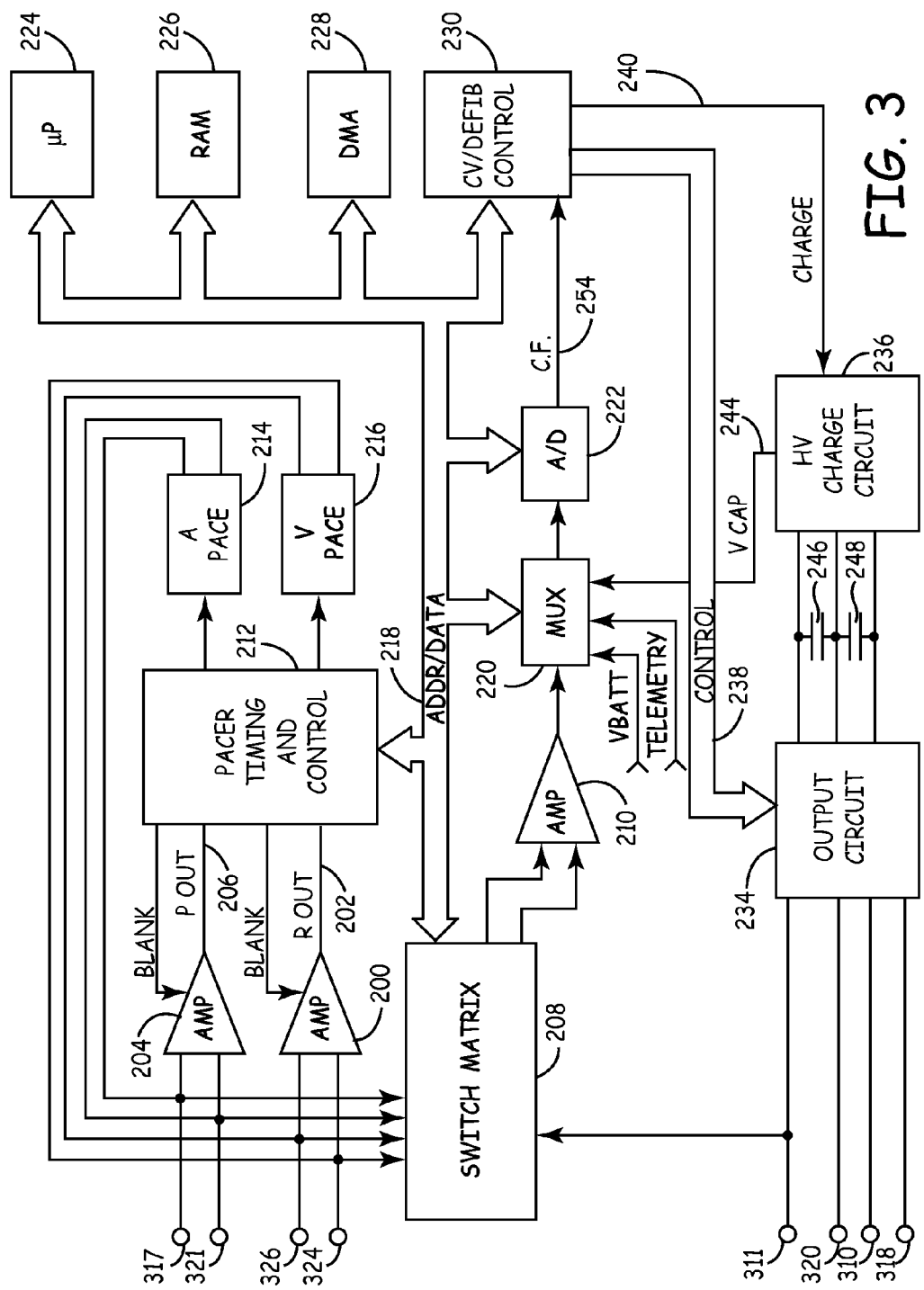
FIG. 3 shows a functional schematic diagram of an implantable pacemaker/cardioverter/defibrillator within which certain embodiments of the invention may be practiced.

With reference to FIG. 3, a functional schematic diagram of an implantable medical device in which certain embodiments of the invention may be practiced is shown. This diagram should be taken as exemplary of the type of device in which certain embodiments of the invention may be embodied, and not as limiting, as it is believed that the invention may usefully be practiced in a wide variety of device implementations, including devices such as cardioverters and defibrillators which do not provide anti-tachycardia pacing therapies, anti-tachycardia pacemakers which do not provide cardioversion or defibrillation, and devices which deliver different forms of anti-arrhythmia therapies such nerve stimulation or drug administration.

The device is provided with a lead system including electrodes, which may be as illustrated in FIG. 2. Alternate lead systems may of course be substituted. If the electrode configuration of FIG. 2 is employed, the correspondence to the illustrated electrodes is as follows.

Electrode 311 corresponds to housing electrode 48, and is the non-insulated portion of the housing of the implantable device. Electrode 320 corresponds to electrode 52 and is a defibrillation electrode located in the right ventricle. Electrode 310 corresponds to electrode 54 and is a defibrillation electrode located in the coronary sinus. Electrode 318 corresponds to electrode 42 and is a defibrillation electrode located in the superior vena cava. Electrodes 324 and 326 correspond to electrodes 30 and 32, and are used for sensing and pacing in the ventricle. Electrodes 317 and 321 correspond to electrodes 46 and 38 and are used for pacing and sensing in the atrium.

Electrodes 310, 311, 318, and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are coupled to the P-wave amplifier 204, which may also take the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5-200 Hz) amplifier 210 for use in digital signal analysis. Selection of electrodes is controlled by the controller or microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present disclosure may correspond to circuitry known in the prior art. An exemplary apparatus is disclosed for accomplishing pacing, cardioversion, and defibrillation functions as follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, P-R intervals and R-P intervals, which measurements are stored in memory 226 and used in conjunction with certain embodiments of the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of certain embodiments of the present invention can include prior art tachyarrhythmia detection algorithms. As described below, the entire ventricular arrhythmia detection methodology of presently available Medtronic pacemaker/cardioverter/defibrillators is employed as part of the arrhythmia detection and classification method according to certain embodiments of the present invention. However, any of the various arrhythmia detection methodologies known to the art might also usefully be employed in alternative embodiments of the present invention.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters. Alternatively, circuitry for controlling the timing and generation of anti-tachycardia pacing pulses as described in U.S. Pat. No. 4,577,633, issued to Berkovits al. on Mar. 25, 1986, U.S. Pat. No. 4,880,005, issued to Pless al. on Nov. 14, 1989, U.S. Pat. No. 7,726,380, issued to Vollmann al. on Feb. 23, 1988 and U.S. Pat. No. 4,587,970, issued to Holley al. on May 13, 1986, all of which are incorporated herein by reference in their entireties may also be used.

In the event that generation of a cardioversion or defibrillation pulse is required, microprocessor 224 employs the escape interval counter to control timing of such cardioversion and defibrillation pulses, as well as associated refractory periods. In response to the detection of atrial requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. Appropriate systems for delivery and synchronization of atrial cardioversion and defibrillation pulses and for controlling the timing functions related to them may be found in PCT Patent Application No. WO92/18198 by Adams et al., published Oct. 29, 1992, and in U.S. Pat. No. 4,316,472 by Mirowski et al., issued Feb. 23, 1982, both incorporated herein by reference in their entireties. In addition, high frequency pulse bursts may be delivered to electrodes 317 and 321 to terminate atrial tachyarrhythmias, as described in PCT Patent Publication No. WO95/28987, filed by Duffin et al. and PCT Patent Publication No. WO95/28988, filed by Mehra et al, both incorporated herein by reference in their entireties.

However, any known cardioversion or defibrillation pulse control circuitry is believed usable in conjunction with certain embodiments of the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375, 817, issued to Engle et al, all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

An example of circuitry, which may be used to control delivery of monophasic pulses, is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in conjunction with a certain embodiments of the present invention for delivery of biphasic pulses.

In modern implantable cardioverter/defibrillators, the physician programs the particular therapies into the device ahead of time, and a menu of therapies is typically provided. For example, on initial detection of an atrial tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher-level cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that fibrillation is identified, high frequency burst stimulation as discussed above may be employed as the initial attempted therapy. Subsequent therapies may be delivery of high amplitude defibrillation pulses, typically in excess of 5 joules. Lower energy levels may be employed for cardioversion. As in the case of currently available implantable pacemakers/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

Currently available implantable cardiac rhythm management devices, including bradycardia and tachycardia pacemakers and cardiac defibrillators, have sense amplifier circuits for amplifying and filtering electrogram signals picked up by electrodes placed in or on the heart and which are coupled by suitable leads to the implantable cardiac rhythm management device. When a pacing pulse is delivered or a natural depolarization occurs in a heart chamber, the resulting potential change appears at the input of the sensing channel for that chamber. In order to prevent saturation of the sense amplifier in this situation, the sensing channel can be blanked for a specified blanking interval by disabling the sense amplifier when a pace is delivered or when a natural depolarization occurs. During the blanking interval, the device thus ignores all electrical activity that appears at the input of the sensing channel. Blanking intervals can be used not only to shield the sensing channel from pacing artifacts, but can also be used to prevent crosstalk between sensing channels where depolarization occurring in one cardiac chamber is interpreted as a depolarization in another chamber. Such crosstalk occurs in the atrial sensing channel when a far-field sense resulting from a ventricular depolarization is interpreted as an atrial sense. Accordingly, a cross-chamber blanking interval for the atrial channel can be provided that is initiated after detection of a ventricular sense.

Because the cross-chamber blanking interval for the atrial sensing channel starts with a ventricular event and lasts for a specified time thereafter, atrial depolarizations occurring shortly after ventricular depolarizations at high ventricular rates may fail to be detected. A cardiac rhythm management device that implements a cross-chamber blanking interval for the atrial sensing channel may thus fail to distinguish an atrial tachyarrhythmia from a ventricular tachycardia. A device might then deliver ventricular anti-tachycardia pacing when atrial anti-tachycardia pacing or an atrial defibrillation shock is actually the appropriate therapy.

In accordance with certain embodiments of the present invention, the atrial cross-chamber blanking interval is shortened when an atrial rate above a specified limit rate is detected. In various embodiments, the blanking interval can be shortened by a predetermined amount or by an amount that varies with the ventricular rate.

Figure 4:
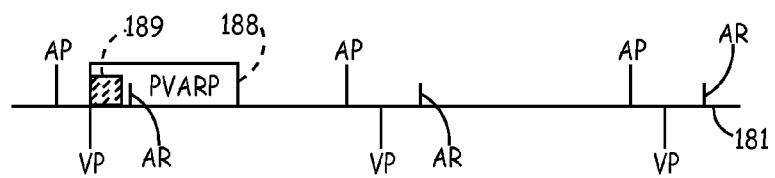
FIGS. 4-6 are marker channel diagrams for simultaneous pacing of both ventricles or single pacing of one ventricle in certain embodiments of the present invention.
Figure 5:
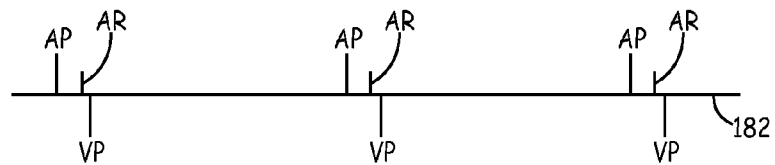

FIGS. 4 and 5 illustrate cases where false atrial tachycardia detection could occur, as shown in these marker channel diagrams (illustrated as lines or graphs 181 and 182). The atrial pace, atrial refractory, and ventricular pace events are simply indicated with AP, AR, and VP, respectively. In FIG. 4 an atrial-sensed event in a post ventricular atrial refractory period (PVARP 188) may be due either to far field R-waves (FFRWs), T-wave sensing, retrograde conduction, skeletal muscle activity artifacts, or any other sense occurring during PVARP, or false atrial sensing due to polarization after a pacing pulse. For heuristic purposes and reference a PVAB period 189 (post ventricular atrial blanking period) is also shown within the PVARP 188 in FIG. 3. In a second case (see FIG. 5), an atrial sense (AR) during the Atrio Ventricular (AV) interval is shown. This may be due to ventricular fusion pacing, loss of atrial capture, junctional rhythm, or any other atrial sense during the AV interval which can fool the tachy detection algorithm by suggesting that the true atrial interval (the interval between the atrial pace events and not the interval between a pace event and a sensed event) is very short.

Far field R-wave sensing may occur in cases other than an AP-AR-AP rhythm. It is also possible to get a far field R-wave after a sinus rhythm, producing an AS-VP-AR marker channel series. While in general it may be assumed that the marker channel diagram of FIG. 4 has appropriately labeled marker signals, these may be incorrect. For example, a far field R-wave or other signal may appear to be something other than it seems. If that is the case, the marker channel generator will label it incorrectly, indicating that the pacemaker may respond incorrectly.

In other pulse generators, there may be no marker channel reference but the device may nonetheless misinterpret signals. The marker channel is used in this description because it is much more easily read than strip charts and because it indicates how the pacemaker is interpreting the sensed signals it is receiving from the heart and its environment.

Figure 6:
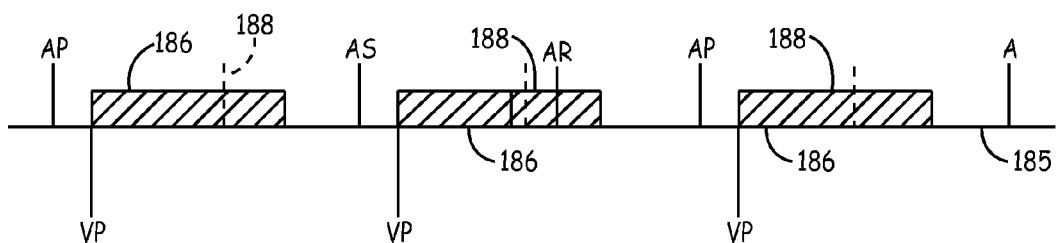

FIG. 6 is a marker channel diagram 185, illustrating PVAB's (post ventricular atrial blanking periods) 186 and also illustrating a blanked atrial refractory sense 188. Starting at the left, the AP-AS (blanked at 188)—AR sequence is interpreted as an A-A interval measured from AP to AS, since the FFRW-type signal at 188 is ignored. Thus, in the case of a long PVAB (Post Ventricular Atrial Blanking period) like PVAB 186, the next marker channel atrial event is further out.

Figure 7A:
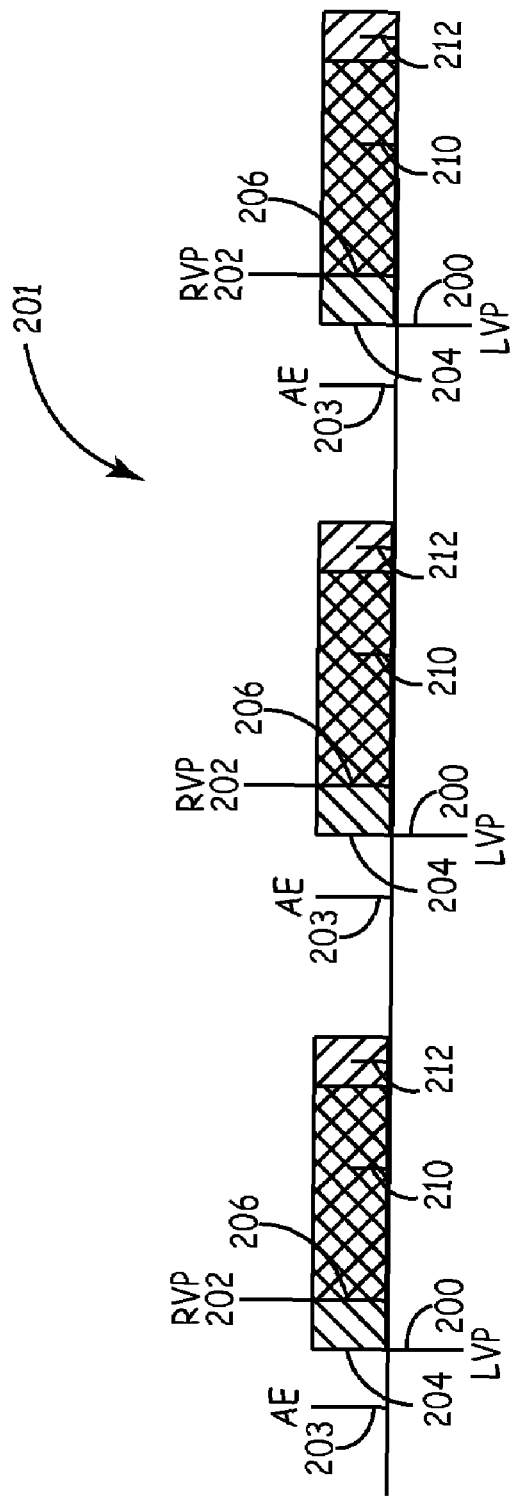
FIG. 7A shows a marker channel diagram for sequential pacing of both ventricles in certain embodiments of the present invention.

With reference to FIG. 7A, a marker channel diagram for sequential pacing (illustrated as lines or graphs 201) of both ventricles in certain embodiments of the present invention is shown. It has been found that sequential pacing of the right and left ventricles instead of simultaneous pacing or single ventricle pacing as shown in FIGS. 4-6 can provide improved hemodynamics. In sequential CRT pacing therapy, the ventricle paces can be separated by as much as 80 ms. As shown in FIG. 7, left ventricle pulse 200 is generally administered first after atrial event 203 (a pacing pulse or a natural depolarization) as the left ventricle is the high pressure side of the heart. Anywhere from 10 ms to 80 ms later a right ventricle pulse 202 is administered to the right ventricle. While this method of sequential CRT pacing has proven to improve hemodynamics of the heart, it also introduces multiple (albeit overlapping) blanking periods where typically only one had existed as shown in FIGS. 4-6.

After left ventricle pace 200, a first blanking period 204 begins typically lasting approximately 100 ms. Then at a predetermined time after left ventricle pace 200, right ventricle pace 202 is administered and second blanking period 206 begins typically lasting approximately 100 ms.

This has the effect of extending the total blanking period by up to 80 ms beyond first blanking period 204. Therefore, in effect, there is an additional 80 ms where an atrial arrhythmia would not be detected. For example, atrial event 210 would not be detected within first blanking period 204 and second atrial event 212 would not be detected within second blanking period 206.

Figure 7B:
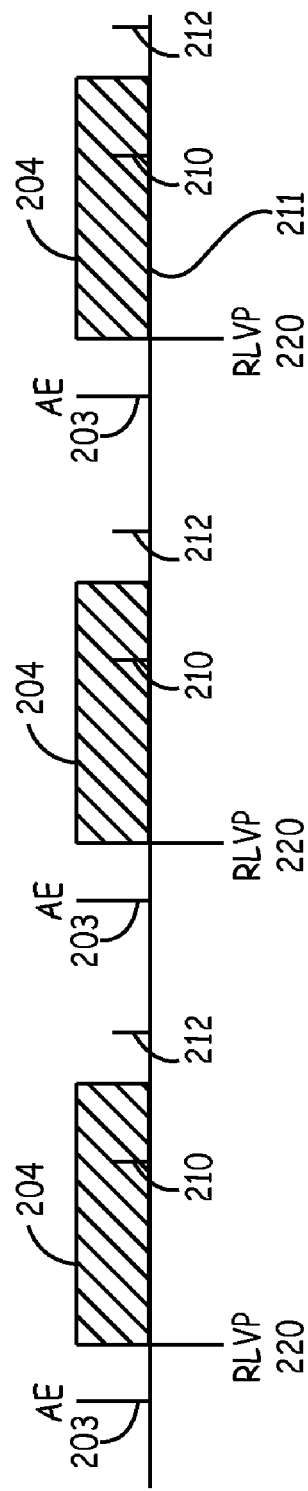
FIG. 7B shows a marker channel diagram for simultaneous or single ventricle pacing in certain embodiments of the present invention.

FIG. 7B shows a marker channel diagram for simultaneous or single ventricle pacing (illustrated as lines or graphs 211) in certain embodiments of the present invention. Upon preliminary detection of an atrial arrhythmia microprocessor 224 mode switches to a confirmation mode B1 (FIG. 8), discussed in more detail below. In the confirmation mode, the left ventricle and right ventricle are simultaneously pulsed with pulse 220 generally administered shortly after an atrial event 203 (a pacing pulse or a natural depolarization). However, it is fully contemplated that one ventricle is paced instead of both without departing from the spirit of the present disclosure. After ventricle pace 220, a first blanking period 204 begins typically lasting approximately 100 ms. by shifting to sequential pacing, second blanking period 206 is eliminated thus reducing the total blanking period. This can have the effect of increasing the ability to detect possible atrial arrhythmias. For example, atrial event 210 would still not be detected within first blanking period 204, however, second atrial event 212 would be detected now that second blanking period 206 is taken away, thus allowing for the detection of atrial even 212.

Figure 7C:
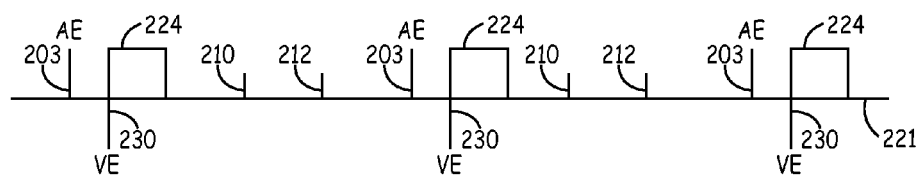
FIG. 7C shows a marker channel diagram for a blanking period during a natural depolarization event in certain embodiments of the present invention.

FIG. 7C shows a marker channel diagram for a blanking period during a natural depolarization event (illustrated as lines or graphs 221) in certain embodiments of the present invention. Upon preliminary detection of an atrial arrhythmia, microprocessor 224 mode switches to a confirmation mode B2 (FIG. 8), discussed in more detail below. In the confirmation mode, the left ventricle and right ventricle are allowed to depolarize intrinsically with depolarization event 230. The ventricles are only paced if no depolarization occurs after a ventricle to ventricle delay from the previous R wave. After ventricle depolarization 230, a shortened blanking period 224 begins typically lasting approximately 30 ms. By shifting to natural or intrinsic depolarization, second blanking period 206 is eliminated and first blanking period 204 is reduced, thus reducing the total blanking period. Therefore, atrial events 210 and 212 are detected, allowing for the detection of an atrial arrhythmia.

Figure 8:
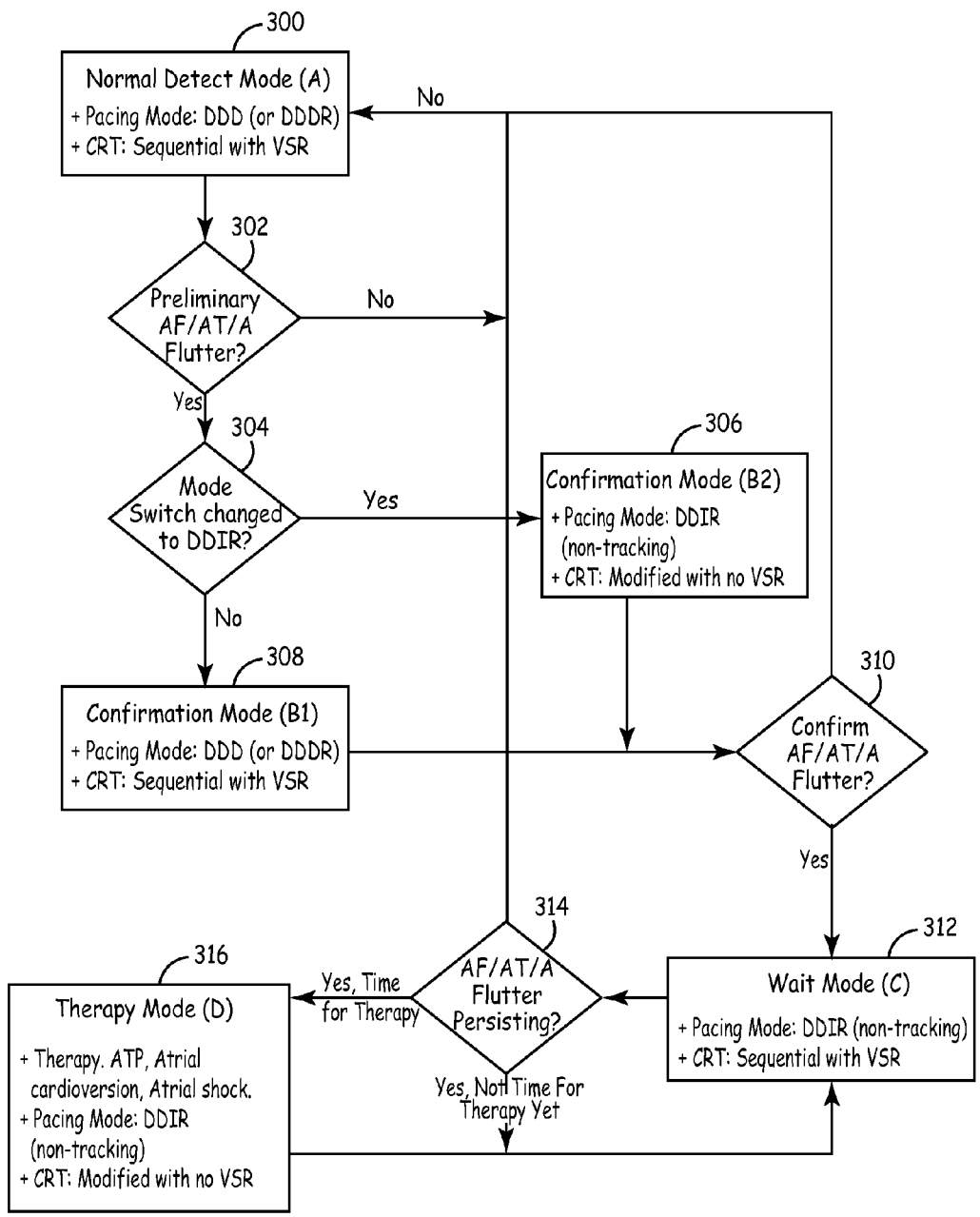
FIG. 8 shows a flow chart diagram of an atrial arrhythmia detection method according to certain embodiments of the present invention.

With reference to FIG. 8, a flow chart diagram of an atrial arrhythmia detection method according to certain embodiments of the present invention is shown. Implantable medical device 10 typically operates in a normal detection mode represented as state 300. In this operating mode IMD 10 operates in a DDD or DDDR pacing mode as is known in the art and described in the incorporated references. The atrium is paced if no contraction of the atrium occurs intrinsically after a period of delay following the previous atrial contraction. In this pacing mode, the ventricles are also paced if no contraction of the ventricles occurs intrinsically. This ventricular pacing occurs after a predetermined atrial-ventricular delay based upon the P wave. In normal detection mode 300, the CRT mode is set to Sequential with VSR (ventricular sense response). That is, the ventricles are paced sequentially separated by a predetermined time. This time period can range from 10 ms to 80 ms depending on which time frame provides the best hemodynamics for the heart. The left ventricle is commonly paced first with the right ventricle paced afterwards. VSR pacing indicates that the ventricles are paced upon sensing a ventricular event. Therefore, not only are the ventricles sequentially paced after a period when no contraction occurs intrinsically, but the ventricles are also sequentially paced upon detection of a ventricular event.

At state 302, microprocessor 224 will continually monitor the sensed events from the atrium to determine whether any atrial arrhythmias exist. There are many methods to detect atrial arrhythmias as discussed above and with the incorporated references and as disclosed in U.S. Pat. No. 5,814,083 herein incorporated by reference in its entirety. In the present embodiment, the timing of atrial pacing, the AV delay and the value of the PVARP parameter in a dual chamber pacemaker are altered to interrupt a pattern of persistent atrial blanking which results in sensing every other atrial event. As stated above, however, extended blanking periods 204 and 206 (see FIG. 7) can hinder atrial arrhythmia detection. Nevertheless, microprocessor continues to monitor the sensed signals from the atrium to determine if an arrhythmia is occurring. In the preliminary atrial arrhythmia detection at state 302, the threshold for determination of atrial arrhythmia is relatively low due to the loss of atrial data due to blanking periods 204 and 206. If no preliminary atrial arrhythmia detection is made, microprocessor 224 returns to state 300 and resumes normal operation. If a possible atrial arrhythmia is detected, microprocessor 224 proceeds to state 304 where a determination is made as to whether the clinician implanting IMD 10 set the device to proceed to a DDIR mode upon preliminary detection of an atrial arrhythmia.

If the mode switch is on, microprocessor 224 proceeds to state 306 where a pacing mode change is made. If the mode switch is off, microprocessor 224 proceeds to state 308 where the pacing mode remains the same. Additionally, the mode switch can be set to on with a delay period. The length of the delay period will often then dictate whether the microprocessor proceeds to state 306 or 308 from state 304. If the delay is set longer than the threshold for preliminary detection of AT/AF/atrial flutter at state 302 (i.e., state 304 requires a longer presence of AT/AF/atrial flutter than state 302), the microprocessor will still see a mode switch set in the "off" position when it passes from state 302 to 304. Accordingly, the microprocessor will switch to state 308. Alternatively, if the delay is shorter than the threshold for preliminary detection of AT/AF/atrial flutter at state 302 (i.e., state 302 requires a longer presence of AT/AF/atrial flutter than state 304), the microprocessor will see a mode switch set in the "on" position when it passes from state 302 to state 304. Accordingly, the microprocessor will switch to state 306 under this scenario.

At state 308, IMD 10 switches to a confirmation mode before determining if an atrial arrhythmia exists at state 310. In this confirmation mode B1, IMD continues to operate in a DDD or DDDR mode. That is, the atrium is paced if no contraction of the atrium occurs intrinsically after a period of delay following the previous atrial contraction. Moreover, as discussed above with reference to state 300, the ventricles are also paced if no contraction of the ventricles occurs intrinsically. This ventricular pacing occurs after a predetermined atrial-ventricular (AV) delay based upon the P wave. In contrast to state 300, though, the CRT pacing is switched to the modified mode without VSR. In this modified mode, the ventricles are not paced upon sensing a ventricular event. Furthermore, the sequential bi-ventricular pacing of state 300 is replaced with simultaneous bi-ventricular pacing (i.e., left and right ventricles paced simultaneously) or single-sided (left or right ventricle) pacing. By eliminating the sequential pacing therapy, blanking period 206 is eliminated, increasing the percentage of the cardiac cycle in which to detect an atrial arrhythmia.

At state 306 (confirmation mode B2), microprocessor 224 switches pacing modes from a DDD or DDDR operation mode to a DDIR. In this "non-tracking" pacing mode, as is known in the art, the ventricles are paced if no contraction of the ventricles occurs intrinsically after a period of delay following the previous ventricular contraction (VV delay based upon the R wave). The atrium may also be paced if no contraction occurs, but this is unlikely given that an atrial arrhythmia has been detected (albeit only preliminarily at state 306). The CRT therapy mode is set to the same as that in state 308—modified with no VSR. Similar to state 308, blanking period 206 is eliminated when removing the sequential pacing therapy, thereby lengthening the time period in which to detect an atrial arrhythmia.

After switching to confirmation state 306 or 308, microprocessor 224 will make a determination and confirm whether an atrial arrhythmia continues to exist at state 310. Unlike the preliminary determination at state 302, the confirmation state of 310 has a higher threshold for atrial arrhythmia determination. This threshold could be similar those disclosed in the references incorporated above. For example, the microprocessor may only require evidence of an atrial arrhythmia to persist for three ventricular cycles before a mode switch occurs—however the episode may need to persist for up to 32 cycles before the atrial arrhythmia is considered sufficiently long to warrant consideration for therapy. Such an example exists in the Medtronic Gem IIII AT Model 7276 defibrillator, where the mode switch criteria is three ventricular beats with evidence of atrial arrhythmia, however the criteria for therapy would be a minimum of 32 ventricular beats with this evidence present. Regardless, if an atrial arrhythmia is not confirmed at state 310, microprocessor 224 returns to state 300 and begins normal detection mode. However, if an atrial arrhythmia is confirmed, microprocessor 224 proceeds to a wait mode at state 312.

At state 312, the pacing mode is set at DDIR mode, like that discussed above for state 306. CRT mode is returned to sequential bi-ventricular with VSR, like that discussed above for state 300. While this reintroduces blanking period 206, this is not a great concern since the arrhythmia has already been detected and therapy has already been scheduled for some later time. That is, at state 312, microprocessor 224 sets a time to administer an atrial therapy.

During the time period before the atrial therapy, microprocessor 224 periodically advances to state 314 where it monitors the sensed atrial signals to determine if the atrial arrhythmia is persisting. Since an atrial arrhythmia has already been detected, the threshold for persisting arrhythmia is low. For comparison sake, the level of arrhythmia for a preliminary detection of atrial arrhythmia is much higher at state 302 than it is at state 314. These algorithms typically employ hysteresis to provide some stability when it is possible that undersensing of the arrhythmia or brief pauses in the arrhythmia may occur. If the atrial arrhythmia has been found to have ceased at state 314, microprocessor 224 returns to normal detection mode at state 300. If the atrial arrhythmia is persisting, but the time for the atrial therapy has not been reached, microprocessor 224 returns to state 312 continuing with the DDIR sequential ventricular pacing mode. If the atrial arrhythmia is persisting and it is time for the atrial therapy, microprocessor 224 proceeds to state 316 switching to an atrial therapy mode.

In the therapy mode at state 316, the pacing mode is set at DDIR and the CRT mode at modified with no VSR. An appropriate atrial therapy is then administered such as a pacing therapy, cardioversion therapy, or a defibrillation therapy. If a defibrillation or cardioversion therapy is administered, the therapy is timed from the ventricle pace or from the first of a sensed ventricle event. Once the atrial therapy is administered, microprocessor 224 returns to the therapy at state 312 and then confirms whether an atrial arrhythmia persists at state 314. If the atrial arrhythmia has ceased, microprocessor 224 returns to normal detection mode at state 300. If the atrial arrhythmia is persisting, a new time for atrial therapy is set. If the time for the atrial therapy has not been reached, microprocessor 224 returns to state 312 continuing with the DDIR sequential ventricular pacing mode. If the atrial arrhythmia is persisting and it is time for the atrial therapy, microprocessor 224 proceeds to state 316 switching to an atrial therapy mode.

After microprocessor 224 determines the presence of an atrial arrhythmia that requires therapy, there are pacing and defibrillation/cardioversion therapy considerations. Delivery of anti-tachy pacing, with occurs at rates similar to the tachycardia itself, should not be followed by CRT with a 1:1 relationship. In addition, the separation of right ventricle and left ventricle paces might interfere with anti-tachy pacing delivery since the IMD circuitry may require time between paces to allow for the capacitor charging and sensing considerations. Thus, during ATP delivery, CRT is modified as noted above to provide single site pacing only or simultaneous right and left ventricle pacing.

For cardioversion/defibrillation, the presence of sequential right and left ventricle pacing may interfere with determining the appropriate "safe" point within which to deliver an atrial therapy. Assuming that IMD 10 will only deliver atrial shocks on ventricular cycle lengths of 500 ms or more, if the right ventricle pace is followed 50 ms later by a left ventricle pace, it is possible to begin the 500 ms window on either the right ventricle or left ventricle pace. If the former, it may not be safe given the time of activation of the left ventricle. If on the latter, it may be unable to synchronize given the large change in rate these small interval adjustments produce at the rate range of interest. One solution as noted above is for the sequential pacing to be suspended before and during cardioversion therapy to permit a more homogeneous depolarization pattern in the ventricles that would provide a safer shock delivery. At the time the shock is to be delivered, and optionally for some number of beats preceding the shock (such as during the charging period) the device could use simultaneous or single-site pacing.

Another improvement to delivery of atrial cardioversion would be the option to synchronize the shock to the right or left ventricle sensed signal. Current ICD's with anti-tachy therapy capability can only sense from the right side of the heart. With left ventricular sensing (and rapidly conducted atrial fibrillation activating the ventricles), the device could selectively synchronize to the left ventricle or right ventricle based on site of the earliest activation. This has the advantage to provide the atrial shock simultaneous with the earliest ventricular activation, understanding in these patients that it is possible with ventricular disynchrony these activations occur at slightly different times.

Thus, embodiments of the DELIVERY OF CRT THERAPY DURING AT/AF TERMINATION are disclosed. The disclosed embodiments are presented for purposes of illustration and not limitation, and the present invention is limited only by the claims that follow.

The invention claimed is:

1. A method for operating a cardiac rhythm management device, comprising:
   sensing atrial depolarizations through an implanted atrial electrode;
   administering a sequential cardiac resynchronization therapy (CRT) pacing therapy in a sequential CRT pacing mode to a left and right ventricle of a heart of a patient via implanted ventricular electrodes in a sequential bi-ventricular fashion;
   detecting an atrial arrhythmia in response to the sensed atrial depolarizations according to a first threshold for determination of atrial arrhythmia;
   switching from the sequential CRT pacing mode to a simultaneous CRT pacing mode in response to detecting the atrial arrhythmia according to the first threshold;
   administering a simultaneous CRT pacing therapy in the simultaneous CRT pacing mode to the left and right ventricle in a simultaneous bi-ventricular fashion; and
   analyzing the sensed atrial depolarizations during the simultaneous CRT pacing therapy to confirm the presence of the detected atrial arrhythmia according to a second threshold for determination of the atrial arrhythmia, the second threshold higher than the first threshold.

2. The method of claim 1, further including analyzing the sensed atrial depolarizations while in the sequential CRT pacing mode to detect the presence of atrial arrhythmia.

3. The method of claim 1, further including sensing ventricular depolarizations of the left and the right ventricle.

4. The method of claim 1, further including providing an atrial pacing therapy when no atrial depolarizations are sensed for a predetermined amount of time.

5. The method of claim 1, further including switching from the simultaneous CRT pacing mode to the sequential CRT pacing mode when the presence of atrial arrhythmia is not detected.

6. The method of claim 1, wherein switching from the simultaneous CRT pacing mode to the sequential CRT pacing mode further comprises switching to no ventricular sense response.

7. The method of claim 1 further comprising:
   switching to a therapy CRT mode in response to confirming the detected atrial arrhythmia, the therapy CRT mode including one of a single-sided CRT pacing mode and a simultaneous CRT pacing mode, the therapy CRT mode further comprising no ventricular sense response; and
   delivering an atrial therapy during the therapy CRT mode.

8. A method for operating a cardiac rhythm management device, comprising:
   administering a sequential cardiac resynchronization therapy (CRT) pacing therapy in a sequential CRT pacing mode to a left and right ventricle of a heart of a patient via implanted ventricular electrodes in a sequential bi-ventricular fashion;
   detecting an atrial arrhythmia according to a first threshold for determination of atrial arrhythmia;
   switching from the sequential CRT pacing mode to a modified CRT pacing mode in response to the detected atrial arrhythmia;
   administering a modified CRT pacing therapy in the modified CRT pacing mode, the modified CRT pacing therapy being one of a simultaneous CRT pacing therapy and a single-sided pacing therapy, the simultaneous CRT pacing therapy being administered to the left and right ventricle in a simultaneous bi-ventricular fashion, the single-sided CRT pacing therapy being administered to one of the left and right ventricles;
   confirming the detected atrial arrhythmia according to a second threshold for determination of atrial arrhythmia during administration of the modified CRT therapy, the second threshold higher than the first threshold; and
   administering an atrial electrical stimulation therapy via an implanted atrial electrode to an atrium of the patient in the presence of an atrial arrhythmia.

9. The method of claim 8, wherein the atrial electrical stimulation therapy includes at least one of anti-tachy pacing, atrial cardioversion, and atrial defibrillation.

10. The method of claim 8, further including sensing atrial depolarizations.

11. The method of claim 8, wherein switching from the sequential CRT pacing mode to the modified CRT pacing mode occurs before administering the atrial electrical stimulation therapy.

12. The method of claim 8, further including sensing ventricular depolarizations of the left and the right ventricle, and wherein the sequential CRT pacing therapy is applied upon sensing depolarization of the right or left ventricle.

13. The method of claim 8, further including sensing ventricular depolarizations of the ventricles, and wherein one of the sequential CRT pacing therapy and the modified pacing therapy is administered when no ventricular depolarizations are sensed for a predetermined amount of time.

14. The method of claim 8, further including switching from the modified CRT pacing mode to the sequential CRT pacing mode after administering the electrical atrial stimulation therapy.

15. A system for operating a cardiac rhythm management device, comprising:
   means for sensing atrial depolarizations through an implanted atrial electrode;
   means for administering a sequential cardiac resynchronization therapy (CRT) pacing therapy in a sequential CRT pacing mode to a left and right ventricle of a heart of a patient via implanted ventricular electrodes in a sequential bi-ventricular fashion;
   means for detecting an atrial arrhythmia according to a first threshold for determination of atrial arrhythmia;
   means for switching from the sequential CRT pacing mode to a single-sided CRT pacing mode in response to the detected atrial arrhythmia;
   means for administering a single-sided CRT pacing therapy in the single-sided CRT pacing mode to one of the left and right ventricle; and
   means for analyzing the sensed atrial depolarizations during the single-sided CRT pacing therapy to confirm the presence of the detected atrial arrhythmia according to a second threshold for determination of the atrial arrhythmia, the second threshold higher than the first threshold.

16. The system of claim 15, further including means for analyzing the sensed atrial depolarizations while in the sequential CRT pacing mode to detect the presence of atrial arrhythmia.

17. The system of claim 16, wherein the analysis to detect the presence of an atrial arrhythmia while in the sequential CRT pacing mode is a preliminary detection analysis.

18. The system of claim 15, further including sensing ventricular depolarizations of the ventricles.

19. The system of claim 15, further including providing an atrial pacing therapy when no atrial depolarizations are sensed for a predetermined amount of time.

20. The system of claim 15, further including switching from the single-sided CRT pacing mode to the sequential CRT pacing mode when the presence of atrial arrhythmia is not detected.

21. The system of claim 15, wherein the means for switching from the sequential CRT pacing mode to the single-sided CRT pacing mode comprises means for switching to no ventricular sense response.

22. A method for operating a cardiac rhythm management device, comprising:
   sensing atrial depolarizations through an implanted atrial electrode;
   administering a sequential cardiac resynchronization therapy (CRT) pacing therapy in a sequential CRT pacing mode to a left and right ventricle of a heart of a patient via implanted ventricular electrodes in a sequential bi-ventricular fashion;
   detecting an atrial arrhythmia in response to the sensed atrial depolarizations according to a first threshold for determination of the atrial arrhythmia;
   switching from the sequential CRT pacing mode to a modified CRT pacing mode in response to detecting the atrial arrhythmia, the modified CRT pacing mode corresponding to a reduced total atrial blanking period;
   administering the modified CRT pacing therapy; and
   analyzing the sensed atrial depolarizations during the modified CRT pacing mode to confirm the presence of the detected atrial arrhythmia according to a second threshold for determination of the atrial arrhythmia, the second threshold higher than the first threshold.

* * * * *